(12) United States Patent
Fuchs et al.

(10) Patent No.: US 10,685,255 B2
(45) Date of Patent: Jun. 16, 2020

(54) WEAKLY SUPERVISED IMAGE CLASSIFIER

(71) Applicant: Memorial Sloan Kettering Cancer Center, New York, NY (US)

(72) Inventors: Thomas Fuchs, New York, NY (US); Gabriele Campanella, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/432,874

(22) Filed: Jun. 5, 2019

(65) Prior Publication Data

US 2019/0286936 A1 Sep. 19, 2019

Related U.S. Application Data

(63) Continuation of application No. PCT/US2018/042178, filed on Jul. 13, 2018.
(Continued)

(51) Int. Cl.
*G06K 9/62* (2006.01)
*G16H 30/40* (2018.01)
(Continued)

(52) U.S. Cl.
CPC .............. *G06K 9/6211* (2013.01); *G06K 9/62* (2013.01); *G06K 9/6218* (2013.01);
(Continued)

(58) Field of Classification Search
None
See application file for complete search history.

(56) References Cited

U.S. PATENT DOCUMENTS

| 2013/0272548 A1* | 10/2013 | Visser | G06K 9/00624 381/122 |
| 2016/0180151 A1* | 6/2016 | Philbin | G06K 9/00288 382/118 |
| 2017/0053398 A1* | 2/2017 | Mahoor | G06T 7/0012 |

FOREIGN PATENT DOCUMENTS

| CN | 106682233 A * | 5/2017 | |
| WO | WO-2007/131311 A2 | 11/2007 | |
| WO | WO-2007131311 A2 * | 11/2007 | G06F 16/951 |

OTHER PUBLICATIONS

Liu Z, Li Z, Zhang J, Liu L. Euclidean and Hamming Embedding for Image Patch Description with Convolutional Networks. In 2016 IEEE Conference on Computer Vision and Pattern Recognition Workshops (CVPRW) Jun. 26, 2016 (pp. 1145-1151). IEEE. (Year: 2016).*

(Continued)

*Primary Examiner* — Vu Le
*Assistant Examiner* — Tracy Mangialaschi
(74) *Attorney, Agent, or Firm* — Foley & Lardner LLP

(57) ABSTRACT

Systems and methods for training and using an image classifier are provided. A plurality of points can be generated from respective patches of images annotated as either a first type or a second type. The points corresponding to the images of the second type can be clustered into two clusters. A first cluster of the two clusters can be identified as closer to the points corresponding to the images annotated as the first type. The points in the first cluster can be assigned to a class positive, the points in the second cluster can be assigned to a class negative, and the points corresponding to the images annotated as the first type can be assigned to an anchor class. A plurality of triplets can be generated based on the points in the various classes. Parameters of an image classifier can be adjusted based on a loss function of the triplets.

20 Claims, 9 Drawing Sheets

Related U.S. Application Data

(60) Provisional application No. 62/532,795, filed on Jul. 14, 2017.

(51) Int. Cl.
*G06N 3/04* (2006.01)
*G06N 3/08* (2006.01)

(52) U.S. Cl.
CPC ......... *G06K 9/6231* (2013.01); *G06K 9/6267* (2013.01); *G06N 3/04* (2013.01); *G06N 3/08* (2013.01); *G16H 30/40* (2018.01)

(56) References Cited

OTHER PUBLICATIONS

Altwaijry H, Veit A, Belongie SJ, Tech C. Learning to Detect and Match Keypoints with Deep Architectures. In BMVC Sep. 2016. (Year: 2016).*
International Search Report and Written Opinion, PCT/US2018/042178, Memorial Sloan Kettering Cancer Center (dated Oct. 1, 2018).

* cited by examiner

WEAKLY SUPERVISED IMAGE CLASSIFIER

CROSS REFERENCES TO RELATED APPLICATIONS

This application is a continuation of PCT/US2018/042178, filed Jul. 13, 2018, which claims the benefit of and priority to U.S. Patent Provisional Application No. 62/532,795, titled "WEAKLY SUPERVISED IMAGE CLASSIFIER," filed Jul. 14, 2017, the entire contents of both of which are incorporated herein by reference.

FIELD OF THE DISCLOSURE

This disclosure generally relates to systems and methods for training and using an image classifier. More particularly, the disclosure relates to systems and methods for training and using a weakly supervised image classifier by applying machine learning techniques to a plurality of annotated images.

BACKGROUND OF THE DISCLOSURE

Image classification can be a costly and tedious process. For some image classification applications, such as those relating to military or medical fields, accurate and reliable classification of images can be very important, and may typically be performed by people having specialized training. It is difficult to accurately and reliably classify certain types of images in an automated fashion.

BRIEF SUMMARY OF THE DISCLOSURE

Methods, systems, and apparatus are provided relating to training an image classifier. Computational image classifier models may have the potential to substantially reduce the work and resources for automated image classification. In general, the term image classification may include a determination of whether an uncategorized input image is of a first type or a second type, where the first and second types are known. In some implementations, the systems and methods of this disclosure can receive an uncategorized input image having a complex set of features that can be represented in a multi-dimensional space. For example, an image may have a large number of pixels (e.g., in the order of $10^6$ or above), and each pixel may have an associated value for each of a plurality of colors, such as red, green, and blue. The systems and methods described further below can learn a lower-dimensional embedding of the input images from weak supervision. In some implementations, images can be divided into a plurality of patches, and the patches can be automatically partitioned into clusters representing the first type and the second type. Such a learned embedding allows for solving an overall classification task for an input image with a simple classifier, such as k-nearest neighbors with respect to the patches that make up the input image. Generally, weak supervision may refer to cases where the slides in the dataset only the overall slide type (e.g., either the first type or the second type) is known. There may be no information relating to a classification for any individual patch of an image. Thus, the techniques of this disclosure contrast with fully supervised learning, where the label of each patch of an image is known and used for training an image classification model.

In some implementations, an image classification model can be trained based on a set of images whose type (e.g., classification) is known. The images can be divided into patches, and libraries of patches can be generated. For example, one library can include patches corresponding to images of the first type, and a second library can include patches corresponding to images of a second type. Training the image classification model can be accomplished with an iterative training process, and a subset of patches can be sampled from each library for every training round. For a given training round, each patch can be converted to a point in a lower-dimensional embedding space using the image classification model, which may be, for example a convolutional neural network.

In some implementations, the points coming from one library can be clustered into two clusters using a clustering algorithm. Of the two clusters, points included in the cluster that has the minimum distance to the points coming from the second library can be assigned to the class positive, and points included in the other cluster can be assigned to the class negative. The points coming from the second library can be treated as an anchor class. Points from the anchor, positive, and negative classes can be sampled to generate triplets, with each triplet including one anchor point, one positive point, and one negative point. A loss function, such as the triplet margin loss, can then be calculated. In some implementations, gradient descent optimization can be used to tune the parameters of the image classification model to minimize the loss function.

Once the classifier is trained, a new image can be received and divided into a plurality of patches. The classifier can make predictions or classifications of the patches. The predictions (e.g., classifications) of all patches of the image can be aggregated to classify the overall image as either the first type or the second type. In addition, the systems and methods described further below can provide a patch-wise segmentation of a whole image for demarcating the features responsible for classifying the image as either the first type or the second type.

The techniques described in this disclosure can have a variety of useful applications. In some implementations, an image classification system as described herein can be used for medical diagnosis. For example, each image can be an image of a pathology slide representing a tissue sample taken from a patient, and each slide can be classified as either benign or tumorous. The slides can be used to train an image classification model that can determine whether an uncategorized input image represents benign tissue or tumorous tissue. Because a tumor typically represents only a small portion of a slide classified as tumorous, it can be difficult for even a trained human to accurately classify such slides. The systems and methods of this disclosure can help to automate such classification, and can also segment images corresponding to tumorous slides, such that the tumorous portions of each slide categorized as tumorous are clearly demarcated. In some other implementations, the techniques of this disclosure can be applied to other types of images. For example, the systems and methods described herein can be used to automatically determine whether a particular object or person is present in an input image, based on a set of training images, which may be satellite images, for example.

One aspect of this disclosure is directed to a method of training an image classifier. The method can include generating, by a device including one or more processors, a plurality of points from respective patches generated from images that are annotated as either a first type or a second type. The method can include clustering, by the device using a clustering algorithm, the points corresponding to the images annotated as the second type into two clusters. The method can include identifying, by the device, a first cluster of the two clusters that is closer to the points corresponding to the images annotated as the first type than a second cluster of the two clusters. The method can include assigning, by the device, the points in the first cluster to a class positive, the points in the second cluster to a class negative, and the points corresponding to the images annotated as the first type to an anchor class. The method can include generating, by the device, a plurality of triplets. Each triplet can include a respective point from the anchor class, a respective point from the class positive, and a respective point from the class negative. The method can include calculating, by the device, a loss function of the plurality of triplets. The method can include adjusting, by the device, parameters of an image classifier based on the loss function.

In some implementations, each patch can be represented by image data in a multi-dimensional space. The method can further include generating, by the device, the plurality of points by converting the image data for each of the patches to a lower-dimensional space using the image classifier. In some implementations, the image classifier can be implemented as a convolutional neural network.

In some implementations, each image can correspond to a respective pathology slide, the images annotated as the first type are identified as benign, and the images annotated as the second type are identified as tumorous. In some other implementations, each image can correspond to a satellite photograph.

In some implementations, the method can include receiving, by the device, image data corresponding to the plurality of images. The step of generating the plurality of points from respective patches of the images can be performed for only a subset of the plurality of images. In some implementations, calculating the loss function of the plurality of triplets can include calculating, by the device, a triplet margin error for the plurality of triplets.

In some implementations, the method can further include determining, by the device, at least one of a blurriness metric or a light level metric for each of the patches. The method also can include discarding, by the device, a subset of patches based on at least one of the blurriness metric or the light level metric of each patch in the discarded subset of patches prior to generating the plurality of points. In some implementations, the method can further include performing, by the device, data augmentation including at least one of a rotation or a color normalization of at least one of the patches, prior to generating the plurality of points.

In some implementations, identifying the first cluster of the two clusters that is closer to the points corresponding to the images annotated as the first type than the second cluster of the two clusters can further include determining, by the device, that a first average Euclidean distance between the points in the first cluster and the points corresponding to the images annotated as the first type is less than a second average Euclidean distance between the points in the second cluster and the points corresponding to the images annotated as the first type.

In some implementations, the method can further include receiving, by the device, an uncategorized input image subsequent to adjusting the parameters of the image classifier. The method can further include dividing, by the device, the input image into a plurality of uncategorized patches. The method can further include determining, by the device, a classification for each uncategorized patch based on the image classifier.

In some implementations, the method can further include aggregating, by the device, the classifications for each uncategorized patch to determine an overall classification for the input image. In some implementations, the method can further include providing, by the device, an output including a patch-wise segmentation of the input image. The patch-wise segmentation of the input image can indicate, for each patch of the input image, an indication of the classification of the patch.

In some implementations, generating the plurality of points from respective patches of images annotated as either the first type or the second type can include identifying a first set of points of the plurality of points. The steps of clustering, identifying the first cluster, assigning the points, generating the plurality of triplets, calculating the loss function and adjusting the parameters of the image classifier can be performed based on the first set of points. The method can further include, responsive to adjusting the parameters of the image classifier based on the first set of points, repeating the steps of clustering, identifying the first cluster, assigning the points, generating the plurality of triplets, calculating the loss function and adjusting the parameters of the image classifier using a second set of points of the plurality of points.

Another aspect of this disclosure is directed to a system for training a model for image classification. The system can include a device having one or more processors. The device can be configured to generate a plurality of points from respective patches generated from images that are annotated as either a first type or a second type. The device can be configured to cluster, using a clustering algorithm, the points corresponding to the images annotated as the second type into two clusters. The device can be configured to identify a first cluster of the two clusters that is closer to the points corresponding to the images annotated as the first type than a second cluster of the two clusters. The device can be configured to assign the points in the first cluster to a class positive, the points in the second cluster to a class negative, and the points corresponding to the images annotated as the first type to an anchor class. The device can be configured to generate a plurality of triplets, each triplet including a respective point from the anchor class, a respective point from the class positive, and a respective point from the class negative. The device can be configured to calculate a loss function of the plurality of triplets. The device can be configured to adjust parameters of an image classifier based on the loss function.

In some implementations, each patch can be represented by image data in a multi-dimensional space. The device can be further configured to generate the plurality of points by converting the image data for each of the patches to a lower-dimensional space using the image classifier. In some implementations, the image classifier can be implemented as a convolutional neural network.

In some implementations, each image can correspond to a respective pathology slide. The images annotated as the first type can be identified as benign and the images annotated as the second type can be identified as tumorous.

In some implementations, the device can be further configured to receive image data corresponding to the plurality of images and to generate the plurality of points from respective patches of the images for only a subset of the plurality of images. In some implementations, the device can be further configured to calculate the loss function of the plurality of triplets by calculating a triplet margin error for the plurality of triplets.

Other aspects of this disclosure are directed to methods and systems for classifying an image using the image classification system described herein. The classification of an image can be an image-wise classification. In some embodiments, the classification of an image can be a patch-wise classification or segmentation. In some embodiments, the image classification system can receive a given image. The image may be unannotated. The image classification system can divide or otherwise derive patches from the image. The image classification system can convert at least a subset of the patches to lower embedded points. The image classification system can then use the lower embedded points and the trained image classifier to classify each of the subset of patches. The aggregate classification of patches can be used to classify the image.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein.

Section B describes embodiments of systems and methods for classifying images.

A. Computing and Network Environment

Figure 1A:
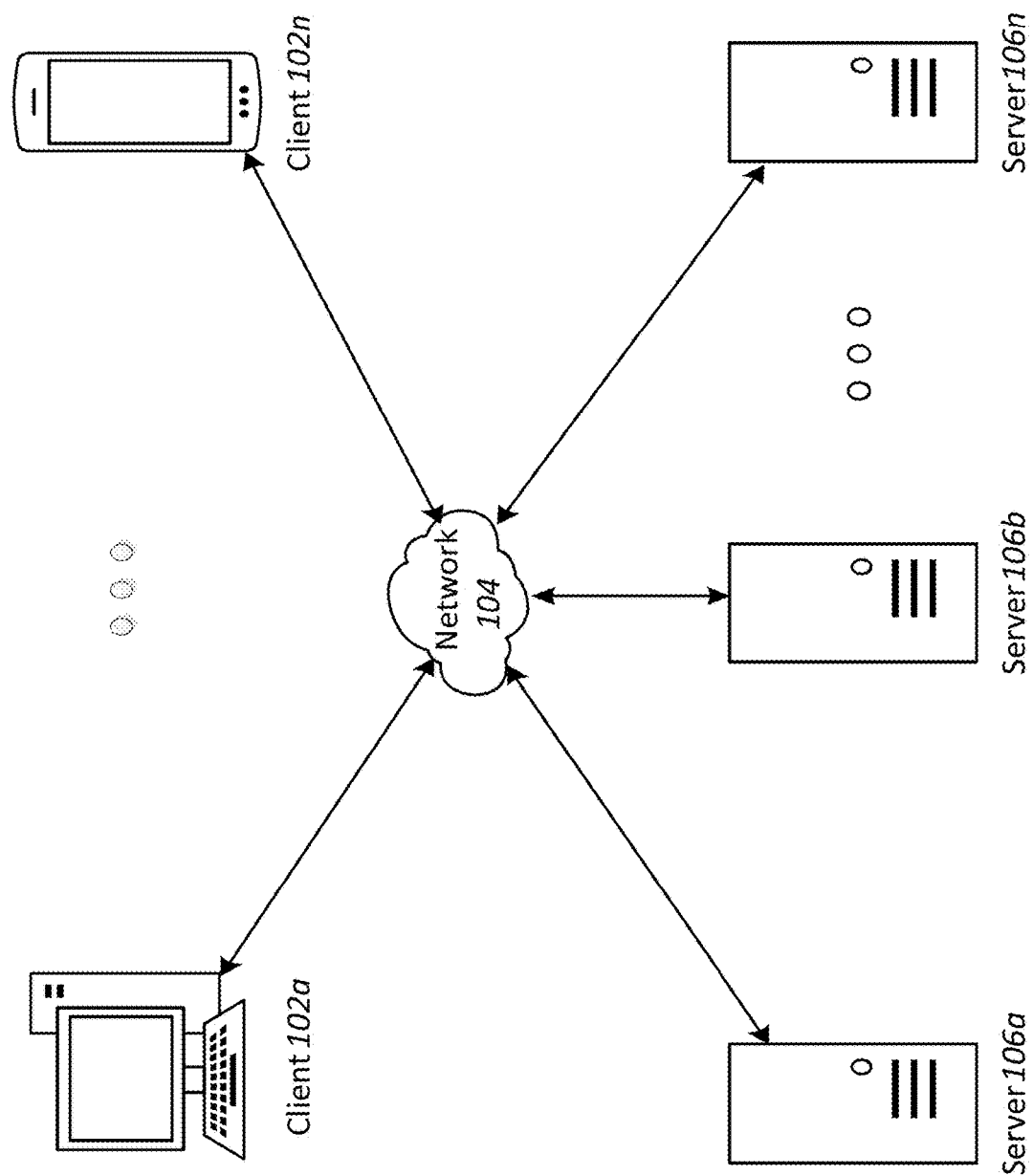
FIG. 1A is a block diagram depicting an embodiment of a network environment comprising a client device in communication with a server device.

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 (not shown) or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALB OX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
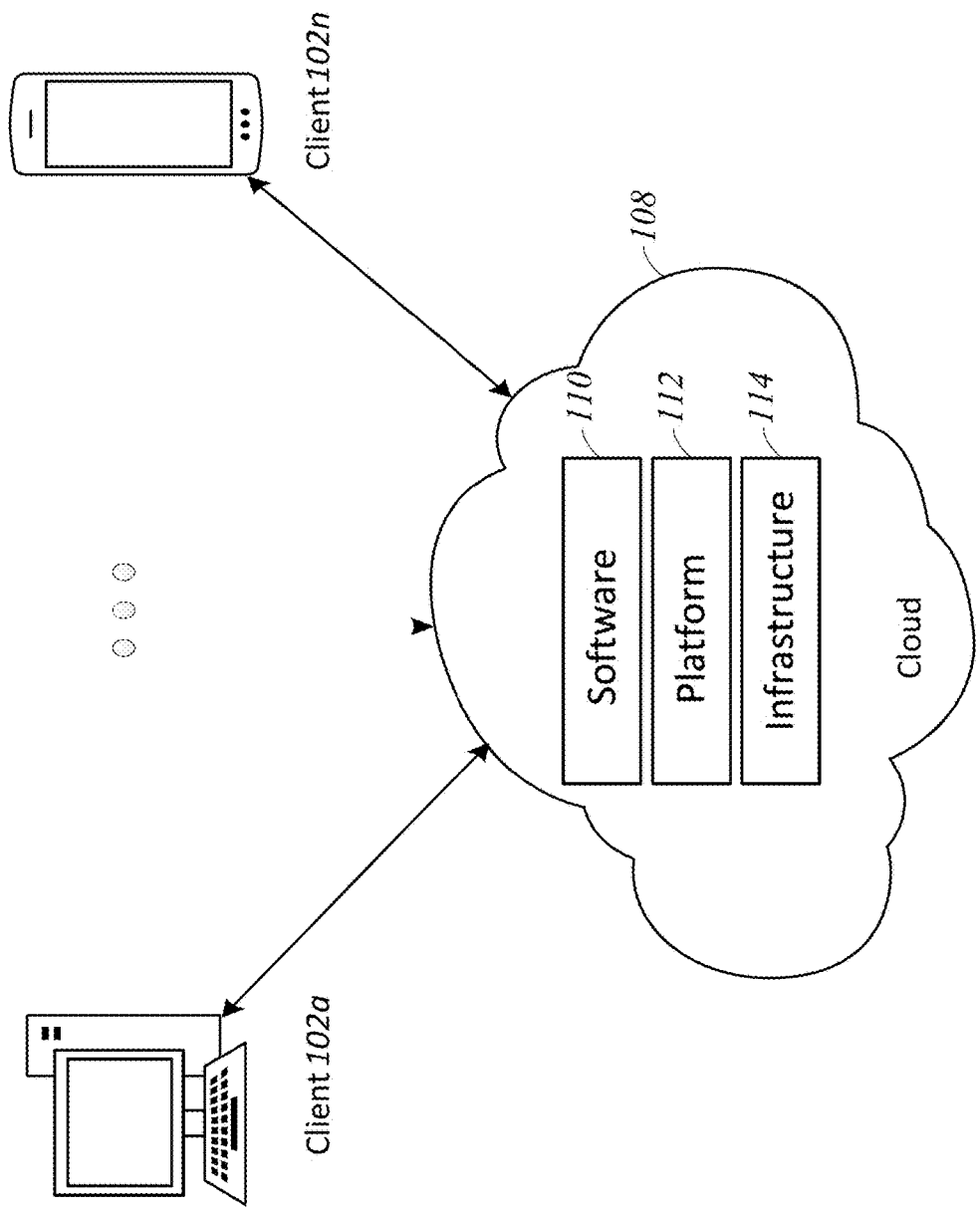
FIG. 1B is a block diagram depicting a cloud computing environment comprising a client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
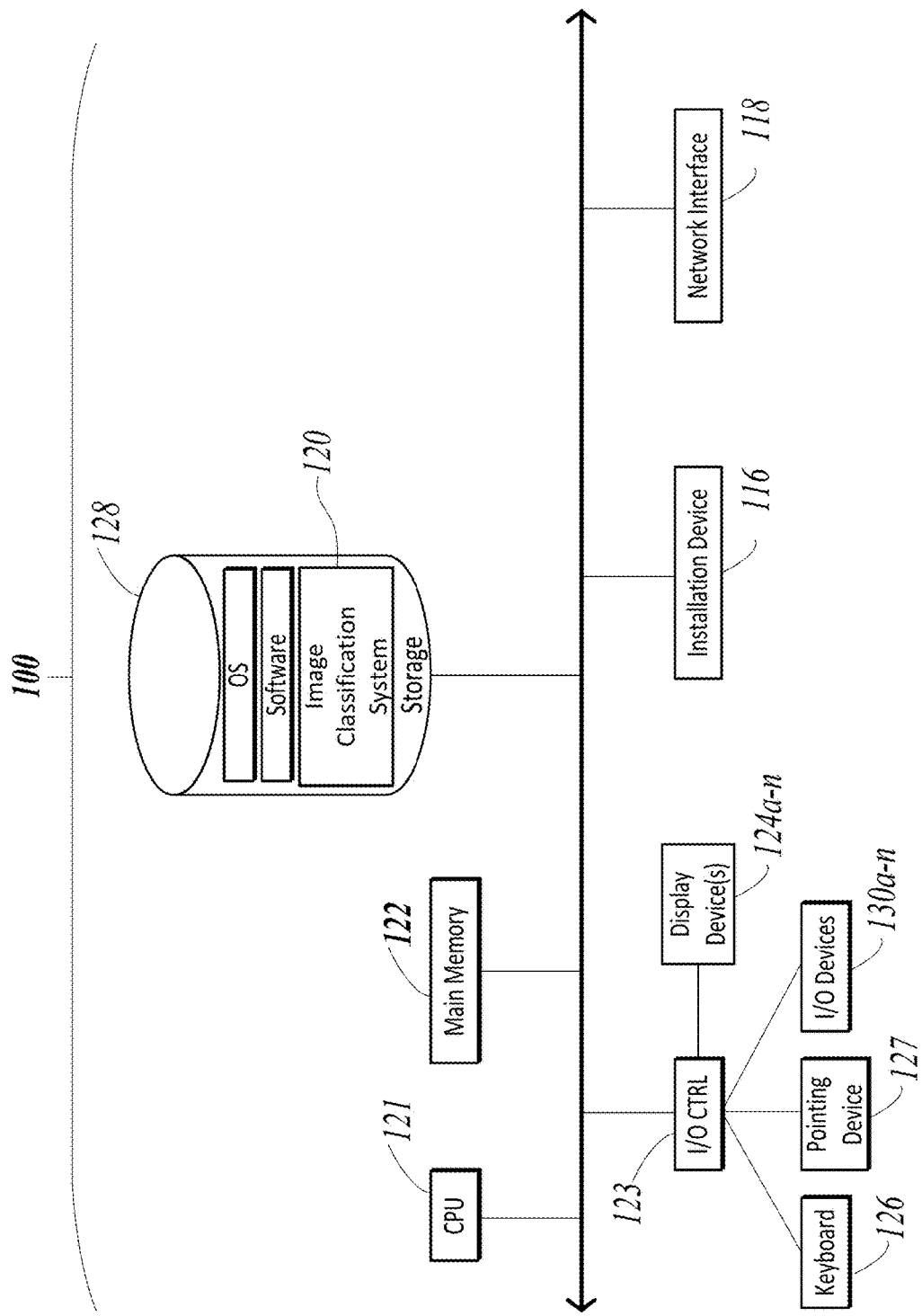
FIGS. 1C and 1D are block diagrams depicting embodiments of computing devices useful in connection with the methods and systems described herein.
Figure 1D:
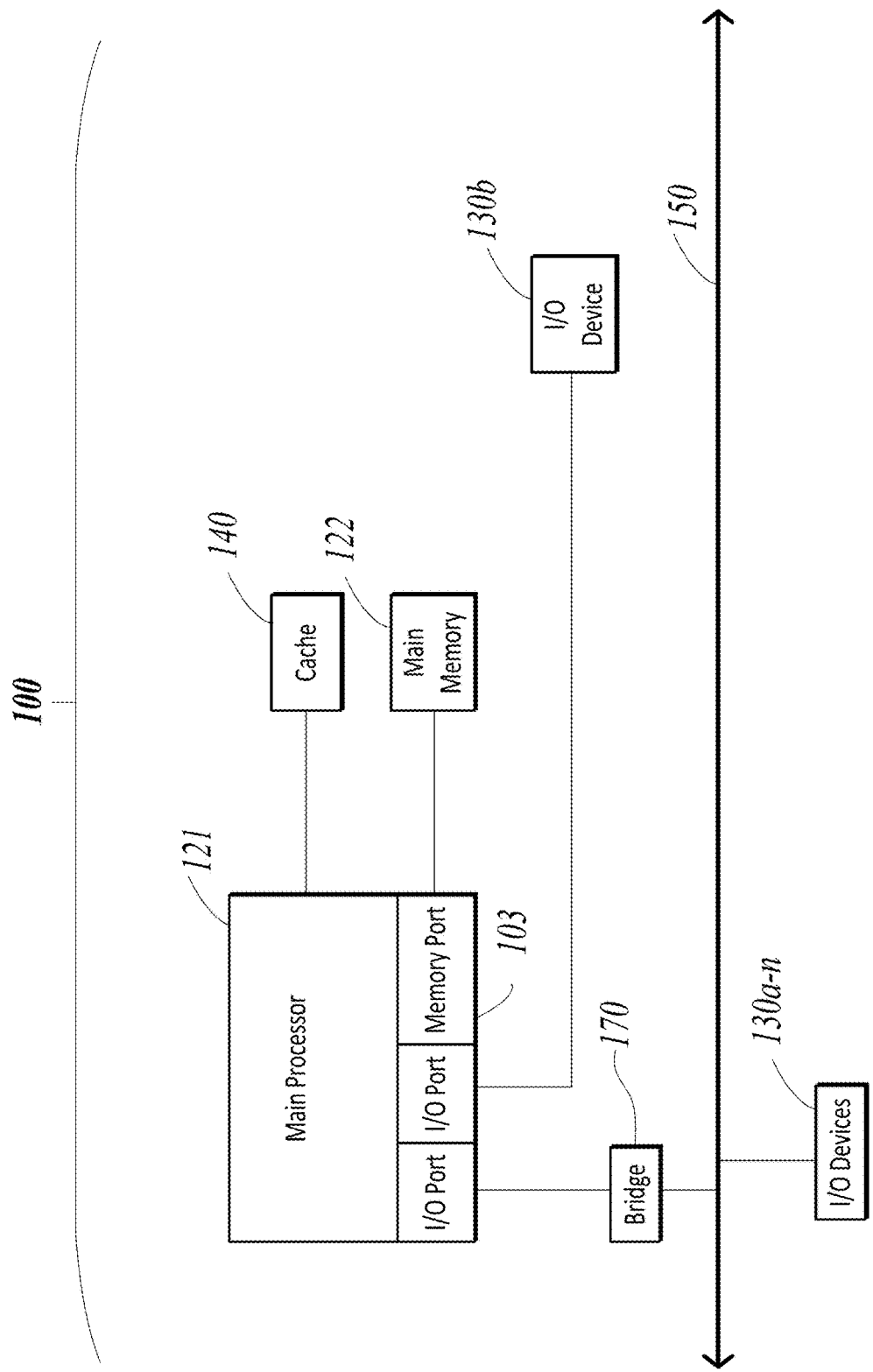

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of an image classification system 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g. those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAIVI), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAIVI), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopic. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the image classification system software 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Systems and Methods for Classifying Images

Methods, systems, and apparatus are provided relating to training an image classifier. Computational image classifier models have the potential to substantially reduce the work and resources needed for automated image classification. In general, the term image classification may include a determination of whether an uncategorized input image is of a first type or a second type, where the first and second types are known. In some implementations, the systems and methods of this disclosure can receive an uncategorized input image having a complex set of features that can be represented in a multi-dimensional space. For example, an image may have a large number of pixels (e.g., in the order of $10^6$ or above), and each pixel may have an associated value for each of a plurality of colors, such as red, green, and blue. The systems and methods described further below can learn a lower-dimensional embedding of the input images from weak supervision. In some implementations, images can be divided into a plurality of patches, and the patches can be automatically partitioned into clusters representing the first type and the second type. Such a learned embedding allows for solving an overall classification task for an input image with a simple classifier, such as k-nearest neighbors with respect to the patches that make up the input image. Generally, weak supervision may refer to cases where the slides in the dataset only the overall slide type (e.g., either the first type or the second type) is known. There may be no information relating to a classification for any individual patch of an image. Thus, the techniques of this disclosure contrast with fully supervised learning, where the label of each patch of an image is used for training an image classification model.

In some implementations, an image classification model can be trained based on a set of images whose type (e.g., classification) is known. The images can be divided into patches, and libraries of patches can be generated. For example, one library can include patches corresponding to images of the first type, and a second library can include patches corresponding to images of a second type. Training the image classification model can be accomplished with an iterative training process, and a subset of patches can be sampled from each library for every training round. For a given training round, each patch can be converted to a point in a lower-dimensional embedding space using the image classification model, which may be, for example a convolutional neural network.

In some implementations, the points coming from one library can be clustered into two clusters using a clustering algorithm. Of the two clusters, the one that has the minimum distance to the points coming from the second library can be assigned to the class positive, and the other cluster can be assigned to the class negative. The points coming from the second library can be treated as an anchor class. Points from the anchor, positive, and negative classes can be sampled to generate triplets, with each triplet consisting of one anchor point, one positive point, and one negative point. A loss function, such as the triplet margin loss, can then be calculated. In some implementations, gradient descent optimization can be used to tune the parameters of the image classification model to minimize the loss function. Finally the predictions (e.g., classifications) of all patches on an image can be aggregated to classify the overall image as either the first type or the second type. In addition, the systems and methods described further below can provide a patch-wise segmentation of an whole image for demarcating the features responsible for classifying the image as either the first type or the second type.

The techniques described in this disclosure can have a variety of useful applications. In some implementations, an image classification system as described herein can be used for medical diagnosis. For example, each image can be an image of a pathology slide representing a tissue sample taken from a patient, and each slide can be classified as either benign or tumorous. The slides can be used to train an image classification model that can determine whether an uncategorized input image represents benign tissue or tumorous tissue. Because a tumor typically represents only a small portion of a slide classified as tumorous, it can be difficult for even a trained human to accurately classify such slides. The systems and methods of this disclosure can help to automate such classification, and can also segment images corresponding to tumorous slides, such that the tumorous portions of each slide categorized as tumorous are clearly demarcated. In some other implementations, the techniques of this disclosure can be applied to other types of images. For example, the systems and methods described herein can be used to automatically determine whether a particular object or person is present in an input image, based on a set of training images, which may be satellite images, for example.

Figure 2A:
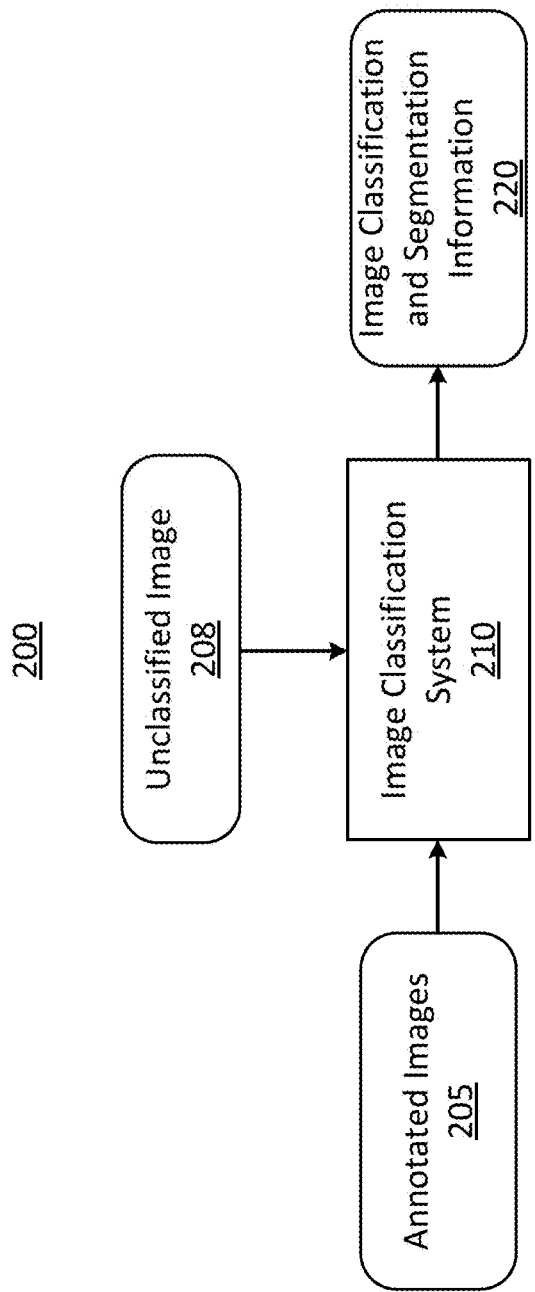
FIG. 2A is a block diagram illustrating the data flow in a system for image classification.

Referring now to FIG. 2A, a block diagram illustrating the data flow in a system 200 for image classification is depicted. The system 200 can include an image classification system 210 configured to receive various annotated and unclassified images, train an image classification model, and use the model to classify and segment an unclassified image. More particularly, the image classification system 210 receives annotated images 205 as well as an unclassified image 208. The annotated images 205 can include any images whose classification is already known, and the annotations of the annotated images 205 can indicate the respective classifications of their images. In a generic example, the annotations may indicate that each annotated image 205 is classified as either a first type or a second type, but it should be understood that the first and second types may be any number of particular classifications in practice. For example, in some implementations the annotated images 205 are pathology slides that are each annotated to indicate whether the slide is classified as benign or tumorous. In some implementations, the image classification system 210 can receive a large number of annotated images 205 (e.g., in the order of $10^4$ or above). For example, the image classification system 210 can receive thousands or millions of annotated images 205.

The image classification system 210 can use the set of received annotated images 205 to train an image classification model. For example, the image classification system 210 can determine the specific characteristics or features of each annotated image 205 that cause an image to have a particular classification, and that information can be incorporated into the image classification model. In some implementations, the image classification model can be implemented using a machine learning algorithm, such as convolutional neural network. After the image classification model has been developed and refined, the image classification system 210 can apply the image classification model to the unclassified image 208 to automatically classify the image. In some implementations, the image classification system 210 also can segment the unclassified image 208 to identify particular portions of the unclassified image 208 that cause the unclassified image 208 to be assigned to a given classification. Stated another way, the image classification system 210 can divide the unclassified image 208 into a plurality of patches, and can further determine a classification for each patch by using the image classification model. Based on the classifications of the patches, the image classification system 210 can determine an overall classification for the image, and can segment the image in a patch-wise fashion to generate the image classification and segmentation information 220. Further implementation details of the image classification system 210 of FIG. 2A are described below in connection with FIGS. 2B and 3.

Figure 2B:
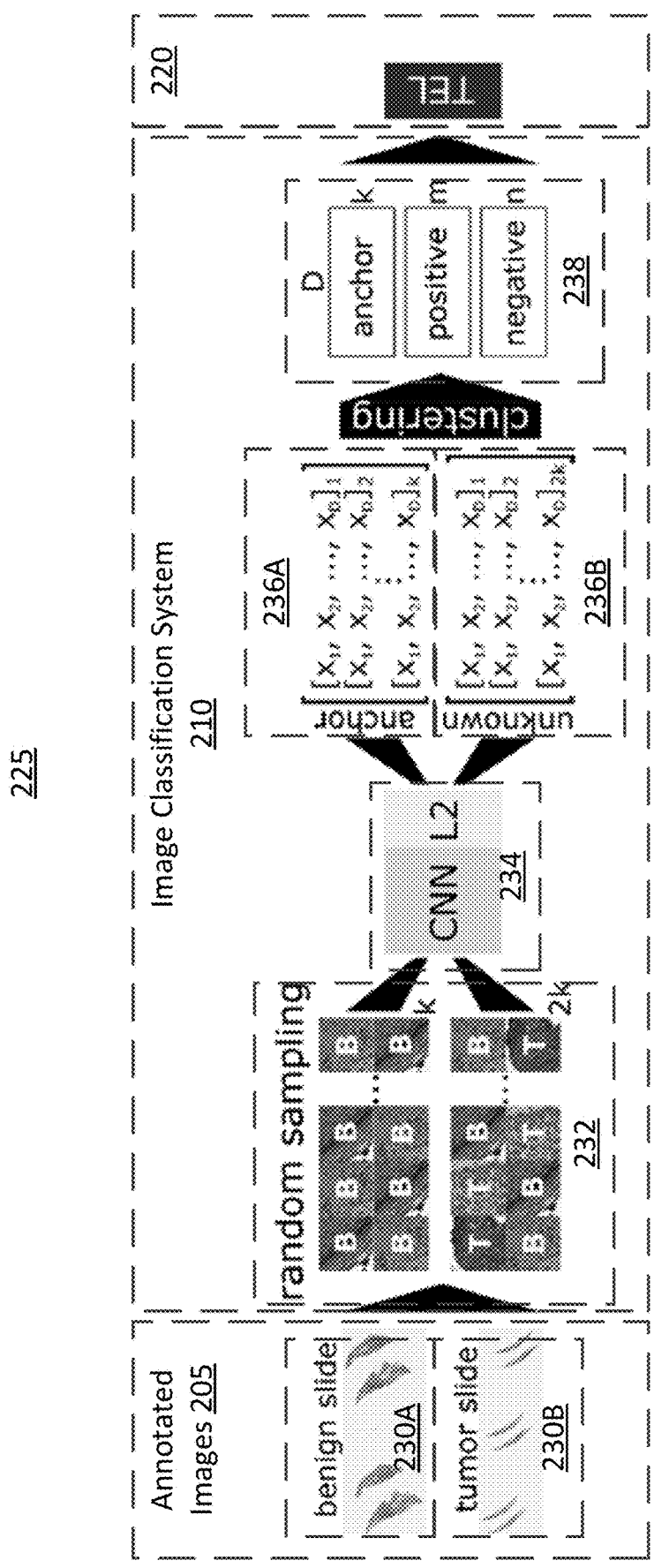
FIG. 2B is a block diagram illustrating the data flow in a system for image classification for pathology slides.

Referring now to FIG. 2B, a block diagram illustrating the data flow in a system 225 for image classification for pathology slides is depicted. The system 225 can include the same components as the system 200 described herein above in conjunction with FIG. 2A. In the system 225, the image classification system 210 can receive annotated images 205 to train an image classification model for pathology. The annotated images 205 can include a set of benign slides 230A and a set of tumorous slides 230B. The set of benign slides 230A can include images of histology slides labeled as having benign tissue. The set of tumorous slides 230B can include images of histology slides labeled as having tumorous tissues. With receipt of the annotated images 205, the image classification system 210 can select or generate a set of random samples 232 of the set of benign slides 230A and the set of tumorous slides 230B. The sampling of the set of benign slides 230A and the tumorous slides 230B can be in accordance with simple random sampling, systematic random sampling, and compressed sensing, among others. The set of random samples 232 can include a k number of samples from the set of benign slides 230A and another k number of samples from the set of tumorous slides 230B. The set 232 can include 2k in total number of samples between the two sets 230A and 230B.

The image classification system 210 can apply the set of random samples 232 to an image classification model 234. In some implementations (such as the one depicted), the image classification model 234 can include a convolutional neural network (CNN) and a norm function (e.g., Euclidean norm). The CNN can include one or more layers (e.g., a convolutional layer, a pooling layer, a rectified linear unit layer, and a fully connected layer, among others) and filters at each layer. The filters of the CNN can include a multiplicative factor to apply to an element of the input, such as the set of random samples 232. By training, the image classification system 210 can adjust or set the filters at each layer of the CNN. With the application of the set of random samples 232 to the CNN and then the norm function of the image classification model 234, the image classification system 210 can generate an output in a feature map. The output can include a set of anchor points 236A and a set of unknown points 236B. The set of anchor values 236A can correspond to data either originally from the set of benign slides 230A and the set of tumorous slides 230B. The output can include a D by k number of data points from the set of anchor points 236A and another a D by k number of data points from the set of unknown points 236B. The output can include a D by 2k number of data points between the two sets 236A and 236B. The number D can depend on the number of layers and filters in the CNN of the image classification model 234.

With the generation of the output from the image classification model 234, the image classification system 210 can apply a clustering algorithm (e.g., k-nearest neighbors clustering) to form triplets 238. The triplets 238 can include a set of anchor data points, a set of positive data points, and a set of negative data points. The set of anchor data points can number D by k. The set of positive data points can number D by m. The set of negative data points can number D by n. The set of positive data points and the negative data points can be determined from the applying the clustering algorithm. Using the triplets 238, the image classification system 210 can calculate a loss function (e.g., triplet loss margin). Based on the value of the loss function, the image classification system 210 can adjust the image classification model 234 (e.g., the filters of the CNN) to reduce or minimize the loss function between the set of positive data points and the set of anchor data points, while maximizing the difference between the set of positive data points and the set of negative data points. The image classification system 210 can iterate the application of the image classification model 234, the clustering algorithm, and the calculation of the loss function until the image classification model 234 is determined to have converged. Once the image classification model 234 is trained, unlabeled pathology slides may be inputted into the image classification system 210 to generate image classification and segmentation information 220. Further implementation details of the image classification system 210 of FIG. 2B are described below in connection with FIG. 3.

Figure 3:
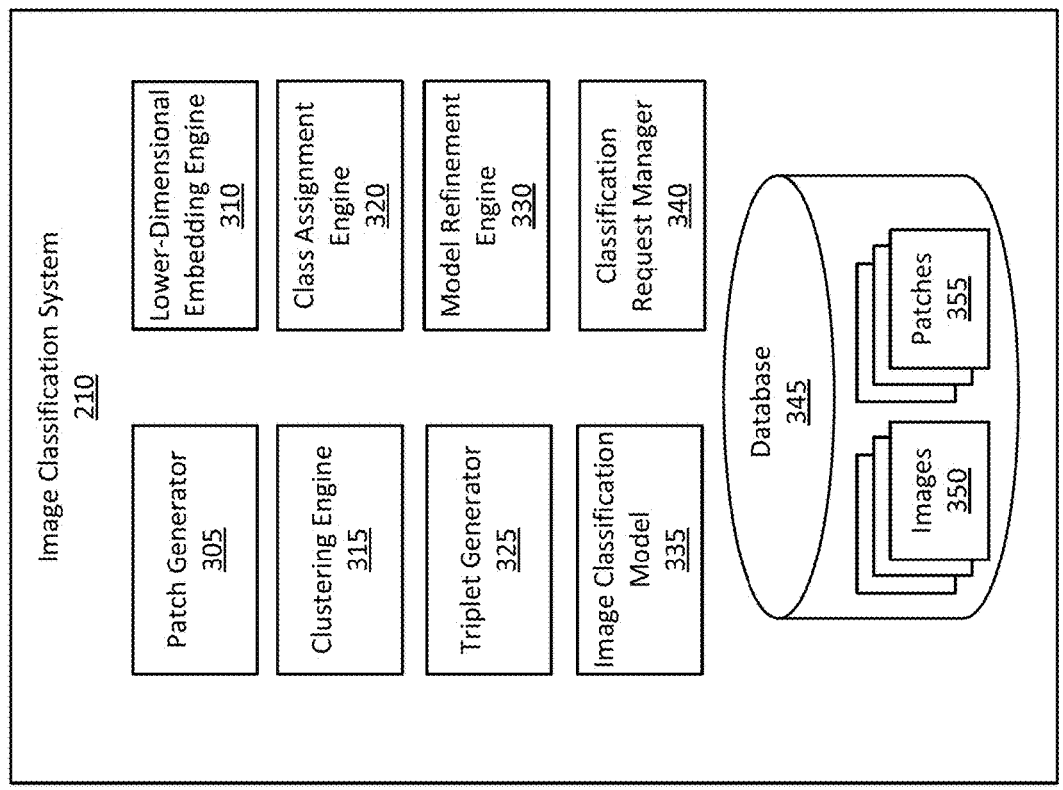
FIG. 3 depicts some of the architecture of an implementation of an image classification system.

FIG. 3 depicts some of the architecture of an implementation of the image classification system 210 shown in FIG. 2A. As described above, the system 210 can receive various annotated and unclassified images, train an image classification model, and use the model to classify and segment an unclassified image. In some implementations, the components of the system 210 shown in FIG. 3 can include or can be implemented using the systems and devices described above in connection with FIGS. 1A-1D. For example, the image classification system 210 and any of its components may be implemented using computing devices similar to those shown in FIGS. 1C and 1D and may include any of the features of those devices, such as the CPU 121, the memory 122, the I/O devices 130a-130n, the network interface 118, etc.

The image classification system 210 can include a patch generator 305, a lower-dimensional embedding engine 310, a clustering engine 315, a class assignment engine 320, a triplet generator 325, a model refinement engine 330, an image classification model 335, a classification request manager 340, and a database 345 storing images 350 and patches 355, among others. Together, the components of the image classification system 210 can be configured to implement the algorithms and other functionality briefly referred to above in connection with FIG. 2A. In some implementations, the patch generator 305, the lower-dimensional embedding engine 310, the clustering engine 315, the class assignment engine 320, the triplet generator 325, the model refinement engine 330, the image classification model 335, the classification request manager 340, and the database 345 can each be implemented as a set of software instructions, computer code, or logic that performs the functionality of each of these components as described further below. In some implementations, these components may instead by implemented by hardware, for example using one or more field programmable gate arrays (FPGAs) and/or one or more application-specific integrated circuits (ASICs). In some implementations, these components can be implemented as a combination of hardware and software.

In some implementations, the image classification system 210 can receive a plurality of images. The received images can include annotated images such as the annotated images 205 shown in FIG. 2A, which may include information relating to a classification of each image. In some implementations, the images may be electronic images represented by pixel data. The annotations for each image can be included, for example, as metadata associated with a computer file for each image. The image classification system 210 also can receive one or more uncategorized images, such as the uncategorized image 208 shown in FIG. 2A, for which classification information is desired. In some implementations, the image classification system 210 can store each of the received images in the database 345 as the images 350.

The patch generator 305 can divide the plurality of images 350 into a plurality of patches. In general, a patch can refer to a portion of an image. For example, each image 350 can be divided into multiple patches. Each patch may be of a certain size and shape (e.g., 50×50 pixels in square shape). In some implementations, the patch generator 305 can divide an image 350 into a plurality of patches by according to a grid overlay. For example, the patch generator 305 can divide an image 350 having a resolution of 1000 pixels by 1000 pixels into patches each representing an adjacent square portion of the image with a resolution of 10 pixels by 10 pixels, thereby creating 10,000 patches for the image 350. In other implementations, the patch generator 305 can generate the patches in a different fashion. For example, the patch generator 305 can generate patches have rectangular or irregular shapes. In some implementations, the patches may not all have a uniform size, and in some implementations, at least some patches may overlap with portions of other patches for the same image 350. Stated another way, a portion of an image 350 may be included within more than one patch for that image 350. In some implementations, the patch generator 305 can also provide data augmentation and quality control functionality by further processing the generated patches. For example, the patch generator 305 can discard patches that are deemed to be of low quality. In some implementations, the patch generator 305 can determine that a patch is of low quality if the patch is too blurry or too dark to be meaningfully processed. Thus, the patch generator 305 can determine a blurriness metric or a light level metric for each patch, and can discard some of the patches based on the respective blurriness metrics and light level metrics. In some implementations, the patch generator 305 can provide data augmentation by applying one or more image processing techniques to some or all of the patches. For example, the patch generator 305 can apply a color normalization to some or all of the patches, or can spatially rotate some or all of the patches. The patch generator 305 can store the generated patches in the database 345 as the patches 355. In some implementations, the patch generator 305 can select a subset of the generated patches 355 for storage in the database 345 and for further processing. In some implementations, the patch generator 305 can randomly sample or select the subset of generator patches 355. For example, the patch generator 305 can use a pseudo-random number generator to calculate index numbers of patches 355 to select. In this manner, the number of patches 355 analyzed or processed by the image classification system 210 can be reduced.

The lower-dimensional embedding engine 310 can generate a plurality of points from patches of annotated images. As described above, each image may be represented by a set of image data. The image data for each image can be relatively complex. For example, a single image can be represented by data corresponding to thousands or millions of pixels, and each pixel can be represented by a value for several colors, such as red, green, and blue. Thus, an image can be thought of as a point defined in a multi-dimensional space, in which the dimensions correspond to individual pixel positions, color values for each pixel, etc. The lower-dimensional embedding engine 310 can generate points for each patch. In some implementations, the lower-dimensional embedding engine 310 can accomplish this by representing each patch with the same level of granularity used to represent an entire image. Thus, a patch can be represented as a point in a multi-dimensional space having dimensions corresponding to the pixel positions within the patch and the color values for each pixel in the patch. In some other implementations, the lower-dimensional embedding engine 310 can reduce the dimensionality of each patch, for example by applying one or more image transformation techniques to the patches.

After the patches have been generated and represented as points, the image classification system 210 can select a first subset of patches to be used for training the image classification model 335. As described above, there may be thousands or millions of images 350, and each image may be divided into tens, hundreds, thousands, or millions of patches. Because the iterative steps described below for training the image classification model 335 may be computationally intensive, it can be more efficient to process only a subset of the available patches in each iteration. In some implementations, the image classification system 210 can select a predetermined number of patches for each iteration, which may be expressed as a fraction of the available patches based on a desired number of iterations. In some implementations, the image classification system 210 can select the predetermined number of patches randomly (e.g., using simple random or systematic random sampling techniques). For example, if 100 iterations of the iterative training process are to be performed, the image classification system 210 can select the subset of patches for each iteration to be equal to 1% of the total number of available patches, such that all of the patches can be used after all iterations have been performed.

As described above, each annotated image can be classified as either a first type or a second type. From among the selected subset of patches, the clustering engine 315 can cluster the points that correspond to patches of images identified as the second type into two clusters. In some implementations, the clustering engine 315 can use any type of clustering algorithm (e.g., a k-means clustering algorithm, a mean-shift clustering algorithm, an expectation-maximization algorithm, and a hierarchical clustering algorithm) to perform this clustering operation. After the clustering engine 315 clusters the points that correspond to patches of images identified as the second type, the clustering engine 315 can identify a first cluster of the two clusters that is closer to the points of the images annotated as the first type than the second cluster. Proximity of each cluster to the points of the images annotated as the first type can be measured in a variety of ways. In some implementations, the clustering engine 315 can determine a distance (e.g., rectilinear, Euclidean, or $L^p$ norm) from each cluster to the points of the images annotated as the first type. For example, the clustering engine 315 can determine a first point representing an average of all of the points in the first cluster, a second point representing an average of all of the points in the second cluster, and a third point representing an average of all of the points of the images annotated as the first type. The clustering engine 315 can then determine the distance between the first point and the third point, and the distance between the second point and the third point, and can finally determine that the distance between the first point and the third point is less than the distance between the second point and the third point.

The class assignment engine 320 can assign the points to a variety of classes based on the cluster in which each point exists. For example, the class assignment engine 320 can assign the points of images annotated as the first type to an anchor class. The class assignment engine 320 also can assign the points of the first cluster to a class positive, because of their proximity to the points of the anchor class (e.g., the points of images annotated as the first type) or to a centroid of the anchor class. Similarly, the class assignment engine 320 also can assign the points of the second cluster to a class negative, because they are expected to be farther from the points of the anchor class (on average) than the points of the class positive or farther from the centroid of the anchor class.

The triplet generator 325 can generate a plurality of triplets of the various points. In general, a triplet can be represented as an ordered set of three points. In some implementations, the triplet generator 325 can generate the triplets such that each triplet includes a point from the anchor class, a point from the class positive, and a point from the class negative. In some implementations, the triplet generator 325 is configured to randomly sample from each class to generate the triplets. To create each triplet, the triplet generator 325 can randomly select a first point from the anchor class, randomly select a second point from the class positive, and randomly select a third point from the class negative. In some implementations, the random selection of points for each triplet may be independent. As a result, the triplet generator 325 can generate two or more triplets having at least one common point. For example, a particular point from one of the classes may appear in more than one generated triplet. In some other implementations, the triplet generator 325 can sample from the classes in a manner that ensures no points are repeated across the generated triplets. In some implementations, the triplet generator 325 is configured to select points from each class using any suitable selection algorithm to generate the triplets.

The model refinement engine 330 can use the triplets generated by the triplet generator 325 to calculate a loss function (sometimes referred to as an objective function). In some implementations, the loss function can be a triplet margin error, a mean-squared error, a Bayesian expected loss, and a quadratic loss function, among others. In some other implementations, the model refinement engine 330 can calculate a different type of loss function based on the triplets. In some implementations, the model refinement engine 330 can be further configured to select parameters for the image classification model 335 that minimize or reduce the loss function. For example, in some implementations, the model refinement engine 330 can perform gradient descent optimization on the calculated loss function to determine a set of parameters that can minimize or reduce the loss function. In some other implementations, the model refinement engine 330 can use a different optimization technique to select the parameters to minimize or reduce the loss function. The model refinement engine 330 can then update the image classification model 335 with the selected parameters.

As described above, in some implementations, the process of training the image classification model 335 can be iterative, and can be performed on a plurality of subsets of patches of the annotated images. The image classification model 335 can be an artificial neural network (ANN), a convolution neural network (CNN) (e.g., as detailed herein with the image classification model 234), a support vector machine (SVM), a regression model (e.g., logistic or linear), a Bayesian classifier, and a Markov chain, among others. Thus, in some implementations, the image classification system 210 can determine whether or not all patches have been used to train the model. If there are unused patches remaining, the image classification system 210 can select a new subset of patches, and the clustering engine 315, class assignment engine 320, triplet generator 325, and model refinement engine 330 can repeat the steps described above to further refine the image classification model 335. These steps can be repeated with additional subsets of the available patches until all of the available patches have been used to refine the image classification model 335, such that the image classification model 335 becomes finalized. It should be appreciated that the image classification model 335 may be updated as more and more patches are analyzed and processed. In some implementations, the image classification model 335 may be refined until the loss function generated by triplets is below a predetermined threshold value indicative of an accuracy level of the image classification model.

After the image classification model 335 has been finalized (e.g., reaching convergence), the image classification system 210 can be used to classify an uncategorized input image using the image classification model 335 to determine whether the uncategorized image is of the first type or the second type. In some implementations, the classification request manager 340 can receive a request to classify an input image. The request can include image data corresponding to the uncategorized input image. In some implementations, the image classification model 335 can store the uncategorized input image in the database 345 along with the other images 350.

The patch generator 305 can divide the input image into a plurality of patches, as described above for the annotated images used to train the image classification model 335. For example, the input image can be divided into multiple patches, each of which may be rectangular, square, or irregular in shape. Some of the patches may overlap with portions of other patches for the input image. In some implementations, the patch generator 305 can also discard patches that are deemed to be of low quality, for example if the patches are too blurry or too dark to be meaningfully processed. The patch generator 305 can determine whether the patch is blurry using blur detection techniques. For example, the patch generator 305 can calculate a variance of a Laplacian for the patch. If the variance is greater than a threshold, the patch generator 305 can determine that the patch is too blurry and can discard the patch. On the other hand, if the variance is lower than threshold, the patch generator 305 can determine that the patch is not too blurry and can store the patch for further use. The patch generator 305 can determine whether the patch is dark by calculating the brightness. The patch generator 305 can calculate a brightness of a patch based on an arithmetic mean of the red, blue, and green values on the patch. If the brightness is greater than a threshold, the patch generator 305 can determine that the patch is not dark and can store the patch for further use. Conversely, if the brightness is lower than the threshold, the patch generator 305 can determine that the patch is too dark and can discard the patch. The patch generator 305 also can augment the input image by applying one or more image processing techniques to some or all of the patches of the input image, for example by normalizing the colors of the patches or rotating some of the patches of the input image.

The classification request manager 340 can then determine a classification for each of the patches of the input image. The classification for each patch can be formatted in a manner similar to that of the classification for images as a whole. For example, each patch can be classified as either being of the first type or the second type, based on the similarity of its features or characteristics as compared to those of the annotated images whose classifications are known. In some implementations, the classification request manager 340 can apply the image classification model 335 to each patch of the input image to determine the classification for the patch. Thus, the all of the information relating to the annotated images that has been used to train the image classification model 335 can be used to inform the classification of the patches of the input image.

The classification request manager 340 can then aggregate the classifications of each patch of the input image to determine an overall classification for the input image. In some implementations, a technique or parameter associated with the image classification model 335 can be used to aggregate the classifications of each patch. For example, in some implementations, the classification request manager 340 may determine that the input image should be classified as the second type only if at least a subset of the patches of the input image satisfy a k-nearest neighbors test in which the neighbors of a patch classified as the second type are also determined to be classified as the second type. Otherwise, the input image may be classified as the first type. Thus, in some instances the input image may have one or more patches that are individually classified as the first type, while the input image as a whole is classified as the second type. Similarly, in some instances the input image may have one or more patches that are individually classified as the second type, while the input image as a whole is classified as the first type.

The classification request manager 340 can also provide an output including the classification of the input image, as well as a patch-wise segmentation of the input image. The patch-wise segmentation may include any form of information indicating the positions of each patch of the second type and each patch of the first type. Thus, an observer could determine the portions of the input image that are primarily responsible for the overall classification of the input image.

In one specific example, the annotated images can be pathology slides that are classified as either benign or tumorous, and the input image can be an uncategorized pathology slide whose classification is to be determined to diagnose a subject (e.g., a patient). Using the steps described above, the image classification model 335 can be trained to classify images as either benign or tumorous based on the information included in the annotated input images. Then, the classification request manager 340 can apply the image classification model 335 to the uncategorized input image to determine whether the input image represents benign tissue or tumorous tissue. Furthermore, the classification request manager 340 can provide patch-wise segmentation of the input image showing the particular regions (e.g., locations corresponding to patches) that are tumorous, based on the patches that were individually determined to be tumorous.

Figure 4:
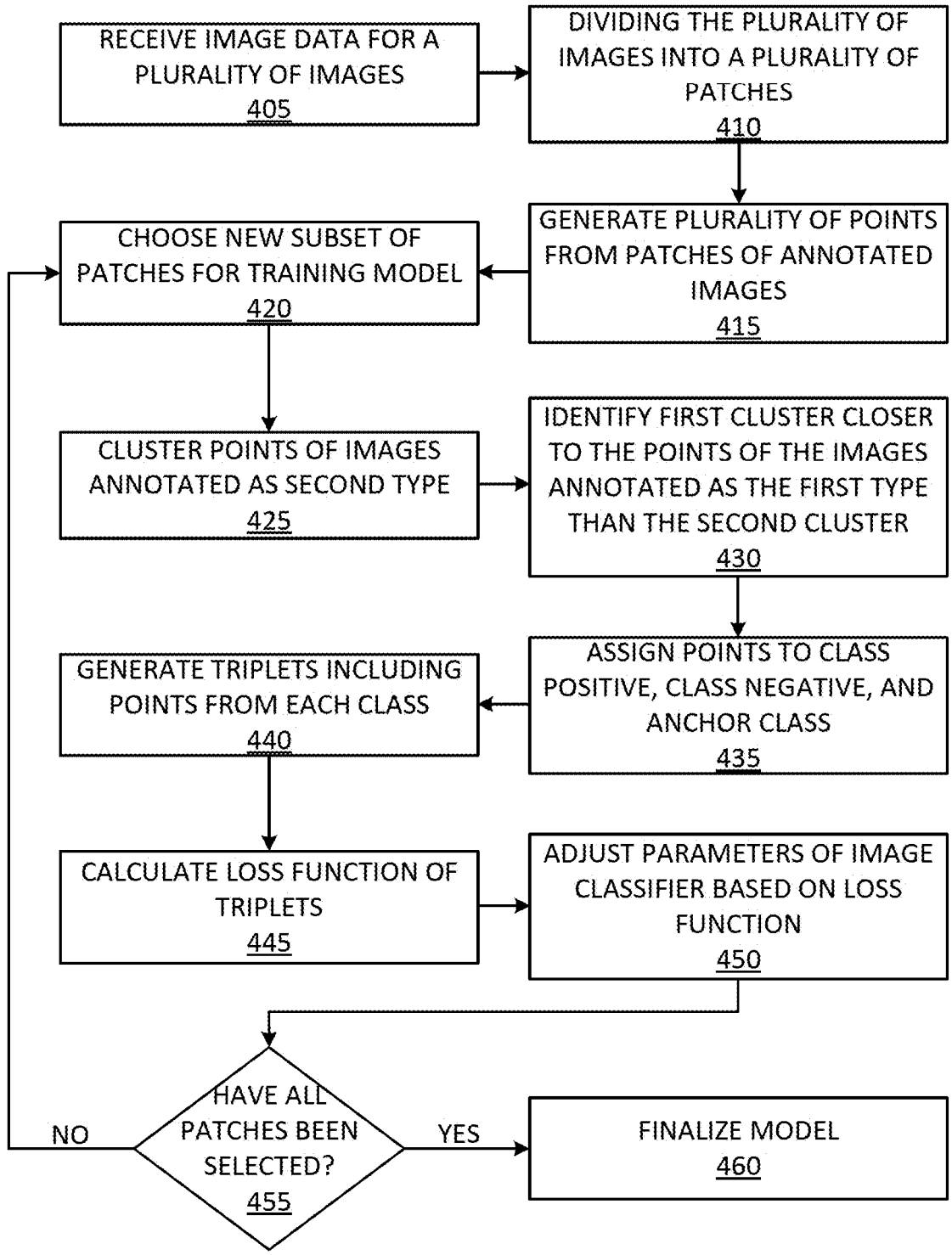
FIG. 4 is a flow chart for an example method of training an image classifier.

FIG. 4 is a flow chart for an example method 400 of training an image classifier. In brief overview, the method 400 includes receiving image data for a plurality of annotated images each classified as a first type or a second type (405), dividing the plurality of images into a plurality of patches (410), generating a plurality of points from patches of annotated images (415), choosing a new subset of patches for training a model (420), clustering points of images annotated as the second type (425), identifying a first cluster closer to the points of the images annotated as the first type than the second cluster (430), assigning the points to a class positive, a class negative, and an anchor class (435), generating triplets each including points from each class (440), calculating a loss function of the triplets (445), and adjusting parameters of an image classifier based on the loss function (450). At 455, if all of the patches have been selected for training the model, the model is finalized (460). Otherwise, the method returns to 420 and a new subset of patches is chosen for training the model.

Referring again to FIG. 4, and in greater detail, the method 400 includes receiving image data for a plurality of annotated images each classified as a first type or a second type (405). In some implementations, this can be performed by an image classification system such as the image classification system 210. In some implementations, the images may be electronic images represented by pixel data. The annotations for each image can be included, for example, as metadata associated with a computer file for each image. In some implementations, the image classification system 210 can store each of the received images in a database.

The method 400 also includes dividing the plurality of images into a plurality of patches (410). In some implementations, this can be performed by a patch generator such as the patch generator 305 shown in FIG. 3. In general, a patch can refer to a portion of an image. For example, each image can be divided into multiple patches. In some implementations, the patch generator can divide an image into a plurality of patches by according to a grid overlay. For example, the patch generator can divide an image having a resolution of 1000 pixels by 1000 pixels into patches each representing an adjacent square portion of the image with a resolution of 10 pixels by 10 pixels, thereby creating 10,000 patches for the image. In other implementations, the patch generator 305 can generate the patches in a different fashion. For example, the patch generator can generate patches have rectangular or irregular shapes. In some implementations, the patches may not all have a uniform size, and in some implementations, at least some patches may overlap with portions of other patches for the same image. Stated another way, a portion of an image 350 may be included within more than one patch for that image.

In some implementations, the patch generator can also provide data augmentation and quality control functionality by further processing the generated patches. For example, the patch generator can discard patches that are deemed to be of low quality. In some implementations, the patch generator can determine that a patch is of low quality if the patch is too blurry or too dark to be meaningfully processed. Thus, the patch generator can determine a blurriness metric or a light level metric for each patch, and can discard some of the patches based on the respective blurriness metrics and light level metrics. In some implementations, the patch generator can provide data augmentation by applying one or more image processing techniques to some or all of the patches. For example, the patch generator can apply a color normalization to some or all of the patches, or can spatially rotate some or all of the patches.

The method 400 also includes generating a plurality of points from patches of annotated images (415). In some implementations, this can be performed by a lower-dimensional embedding engine such as the lower-dimensional embedding engine 310 shown in FIG. 3. As described above, each image may be represented by a set of image data. The image data for each image can be represented by complex data corresponding to thousands or millions of pixels, and each pixel can be represented by a value for several colors, such as red, green, and blue. Thus, an image can be represented as a point defined in a multi-dimensional space, in which the dimensions correspond to individual pixel positions, color values for each pixel, etc. The lower-dimensional embedding engine can generate points for each patch. In some implementations, the lower-dimensional embedding engine can accomplish this by representing each patch with the same level of granularity used to represent an entire image. Thus, a patch can be represented as a point in a multi-dimensional space having dimensions corresponding to the pixel positions within the patch and the color values for each pixel in the patch. In some other implementations, the lower-dimensional embedding engine can reduce the dimensionality of each patch, for example by applying one or more image transformation techniques to the patches.

The method 400 also includes choosing a new subset of patches for training a model (420). The image classification system can select the new subset of patches to be used for training the model, which may correspond to the image classification model image classification model 335 shown in FIG. 3. As described above, there may be thousands or millions of images, and each image may be divided into tens, hundreds, thousands, or millions of patches. Because the iterative steps described below for training the image classification model may be computationally intensive, it can be more efficient to process only a subset of the available patches in each iteration. In some implementations, the image classification system can select a predetermined number of patches for each iteration, which may be expressed as a fraction of the available patches based on a desired number of iterations.

The method 400 also includes clustering points derived from images annotated as the second type (425). In some implementations, this can be performed by a clustering engine such as the clustering engine 315 shown in FIG. 3. The clustering engine can use any type of clustering algorithm to perform this clustering operation. After the clustering engine clusters the points that correspond to patches of images identified as the second type, the clustering engine can identify a first cluster of the two clusters that is closer to the points of the images annotated as the first type than the second cluster (430). Proximity of each cluster to the points of the images annotated as the first type can be measured in a variety of ways. In some implementations, the clustering engine can determine the Euclidean distance from each cluster to the points of the images annotated as the first type. For example, the clustering engine can determine a first point representing an average of all of the points in the first cluster, a second point representing an average of all of the points in the second cluster, and a third point representing an average of all of the points of the images annotated as the first type. The clustering engine can then determine the Euclidean distance between the first point and the third point, and the Euclidean distance between the second point and the third point, and can determine that the distance between the first point and the third point is less than the distance between the second point and the third point.

The method 400 also includes assigning the points to a class positive, a class negative, and an anchor class (435). In some implementations, this can be performed by a class assignment engine such as the class assignment engine 320 shown in FIG. 3. The class assignment engine can assign the points to a variety of classes based on the cluster in which each point exists. For example, the class assignment engine can assign the points of images annotated as the first type to an anchor class. The class assignment engine also can assign the points of the first cluster to a class positive, because of their proximity to the points of the anchor class (e.g., the points of images annotated as the first type). Similarly, the class assignment engine also can assign the points of the second cluster to a class negative, because they are expected to be farther from the points of the anchor class (on average) than the points of the class positive.

The method 400 also includes generating triplets each including points from each class (440). In some implementations, this step can be performed by a triplet generator such as the triplet generator 325 shown in FIG. 3. In general, a triplet can be represented as an ordered set of three points. In some implementations, the triplet generator can generate the triplets such that each triplet includes a point from the anchor class, a point from the class positive, and a point from the class negative. In some implementations, the triplet generator is configured to randomly sample from each class to generate the triplets. That is, to create each triplet, the triplet generator can randomly select a first point from the anchor class, randomly select a second point from the class positive, and randomly select a third point from the class negative. In some implementations, the random selection of points for each triplet may be independent. As a result, the triplet generator can generate two or more triplets having at least one common point. For example, a particular point from one of the classes may appear in more than generated triplet. In some other implementations, the triplet generator can sample from the classes in a manner that ensures no points are repeated across the generated triplets.

The method 400 also includes calculating a loss function of the triplets (445). In some implementations, this can be performed by a model refinement engine such as the model refinement engine 330 shown in FIG. 3. In some implementations, the loss function can be a triplet margin error. In some other implementations, the model refinement engine can calculate a different type of loss function based on the triplets. In some implementations, the model refinement engine can be further configured to select parameters for the image classification model that minimize or reduce the loss function. For example, in some implementations, the model refinement engine can perform gradient descent optimization on the calculated loss function to determine a set of parameters that can minimize or reduce the loss function. In some other implementations, the model refinement engine can use a different optimization technique to select the parameters to minimize or reduce the loss function. The model refinement engine can then update the image classification model by adjusting the parameters of the image classification model with the selected parameters based on the loss function (450).

At 455, if all of the patches have been selected for training the model, the model is finalized (460). Otherwise, the method 400 returns to 420 and a new subset of patches is chosen for training the model. Thus, steps 420, 425, 430, 435, 440, 445, 450, and 455 are iterated until all of the patches have been used to train the image classification model and the model has been finalized.

Figure 5:
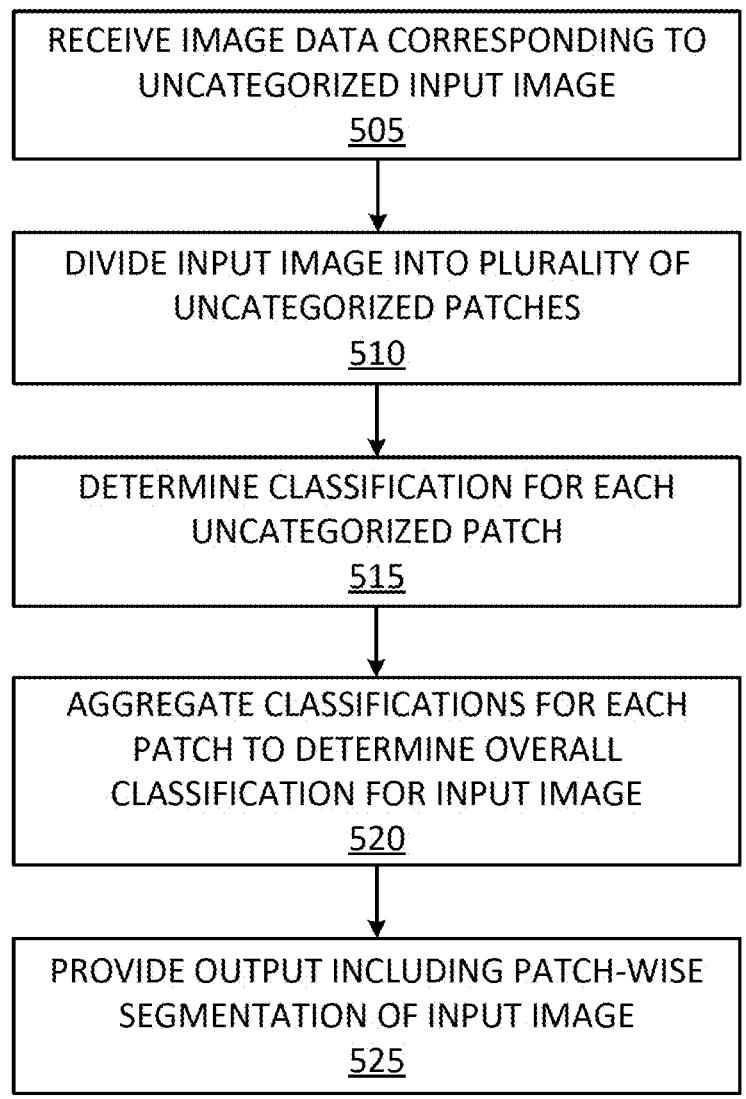
FIG. 5 is a flow chart for an example method of classifying an uncategorized input image.

FIG. 5 is a flow chart for an example method 500 of classifying an uncategorized input image. In brief overview the method 500 includes receiving image data corresponding to an uncategorized input image (505), dividing the input image into a plurality of uncategorized patches (510), determining a classification for each uncategorized patch (515), aggregating the classifications for each patch to determine an overall classification for the input image (520), and providing an output including a patch-wise segmentation of the input image (525).

Referring again to FIG. 5, and in greater detail, the method 500 includes receiving image data corresponding to an uncategorized input image (505). In some implementations, this can be performed by a classification request manager such as the classification request manager 340 shown in FIG. 3. The method 500 also includes dividing the input image into a plurality of uncategorized patches (510). For example, the input image can be divided into multiple patches, each of which may be rectangular, square, or irregular in shape. The patches may be generated by a patch generator such as the patch generator 305 shown in FIG. 3. Some of the patches may overlap with portions of other patches for the input image. In some implementations, the patch generator can also discard patches that are deemed to be of low quality, for example if they are too blurry or too dark to be meaningfully processed. The patch generator also can augment the input image by applying one or more image processing techniques to some or all of the patches of the input image, for example by normalizing the colors of the patches or rotating some of the patches of the input image.

The method 500 includes determining a classification for each uncategorized patch (515). The classification for each patch can be formatted in a manner similar to that of the classification for images as a whole. For example, each patch can be classified as either being of the first type or the second type, based on the similarity of its features or characteristics as compared to those of the annotated images whose classifications are known. In some implementations, the classification request manager can apply the image classification model to each patch of the input image to determine the classification for the patch. Thus, the all of the information relating to the annotated images that has been used to train the image classification model can be used to inform the classification of the patches of the input image.

The method 500 includes aggregating the classifications for each patch to determine an overall classification for the input image (520). In some implementations, a technique or parameter associated with the image classification model can be used to aggregate the classifications of each patch. For example, in some implementations, the classification request manager may determine that the input image should be classified as the second type only if at least a subset of the patches of the input image satisfy a k-nearest neighbors test in which the neighbors of a patch classified as the second type are also determined to be classified as the second type. Otherwise, the input image may be classified as the first type. Thus, in some instances the input image may have one or more patches that are individually classified as the first type, while the input image as a whole is classified as the second type. Similarly, in some instances the input image may have one or more patches that are individually classified as the second type, while the input image as a whole is classified as the first type.

The method 500 includes providing an output including a patch-wise segmentation of the input image (525). In some implementations, this can be performed by the classification request manager. The patch-wise segmentation may include any form of information indicating the positions of each patch of the second type and each patch of the first type. Thus, an observer could determine the portions of the input image that are primarily responsible for the overall classification of the input image.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C #, PROLOG, or in any byte code language such as JAVA. The software programs may be stored on or in one or more articles of manufacture as object code.

While various embodiments of the methods and systems have been described, these embodiments are exemplary and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

What is claimed is:

1. A method of training an image classifier, comprising:
generating, by a device including one or more processors, a plurality of points from respective patches generated from a plurality of images, each image of the plurality of images annotated as one of a first type or a second type, the plurality of images having a first subset of images annotated as the first type and a second subset of images annotated as the second type, the plurality of points comprising a first subset of points corresponding to points generated from the first subset of images and a second subset of points corresponding to points generated from the second subset of images;

selecting, by the device, from the plurality of points, the second subset of points generated from the second subset of images annotated as the second type for clustering;
clustering, by the device using a clustering algorithm, each point of the second subset of points selected from the plurality of points into two clusters;
identifying, by the device, a first cluster of the two clusters having points that are closer to the first subset of points corresponding to the first subset of images annotated as the first type than points of a second cluster of the two clusters;
assigning, by the device, the points in the first cluster to a class positive, the points in the second cluster to a class negative, and the first subset of points corresponding to the first subset of images annotated as the first type to an anchor class;
generating, by the device, a plurality of triplets, each triplet including one of the first subset of points from the anchor class, one of the points from the class positive, and one of the points from the class negative;
calculating, by the device, a loss function of the plurality of triplets; and
adjusting, by the device, parameters of an image classifier based on the loss function.

2. The method of claim 1, wherein each patch is represented by image data in a multi-dimensional space, the method further comprising generating, by the device, the plurality of points by converting the image data for each of the patches to a lower-dimensional space using the image classifier.

3. The method of claim 2, wherein the image classifier is implemented as a convolutional neural network.

4. The method of claim 1, wherein:
each image corresponds to a respective pathology slide;
the images annotated as the first type are identified as benign; and
the images annotated as the second type are identified as tumorous.

5. The method of claim 1, wherein each image corresponds to a satellite photograph.

6. The method of claim 1, further comprising receiving, by the device, image data corresponding to the plurality of images, wherein the step of generating the plurality of points from respective patches of the images is performed for only a subset of the plurality of images.

7. The method of claim 1, wherein calculating the loss function of the plurality of triplets further comprises calculating, by the device, a triplet margin error for the plurality of triplets.

8. The method of claim 1, further comprising:
determining, by the device, at least one of a blurriness metric or a light level metric for each of the patches; and
discarding, by the device, a subset of patches based on at least one of the blurriness metric or the light level metric of each patch in the discarded subset of patches prior to generating the plurality of points.

9. The method of claim 1, further comprising performing, by the device, data augmentation including at least one of a rotation or a color normalization of at least one of the patches, prior to generating the plurality of points.

10. The method of claim 1, wherein identifying the first cluster of the two clusters having the points that are closer to the points corresponding to the images annotated as the first type than the points of the second cluster of the two clusters further comprises:

determining, by the device, that a first average Euclidean distance between the points in the first cluster and the points corresponding to the first subset of images annotated as the first type is less than a second average Euclidean distance between the points in the second cluster and the points corresponding to the first subset of images annotated as the first type.

11. The method of claim 1, further comprising:
receiving, by the device, an uncategorized input image subsequent to adjusting the parameters of the image classifier;
dividing, by the device, the input image into a plurality of uncategorized patches; and
determining, by the device, a classification for each uncategorized patch based on the image classifier.

12. The method of claim 11, further comprising aggregating, by the device, the classifications for each uncategorized patch to determine an overall classification for the input image.

13. The method of claim 12, further comprising:
providing, by the device, an output including a patch-wise segmentation of the input image, the patch-wise segmentation of the input image indicating, for each patch of the input image, an indication of the classification of the patch.

14. The method of claim 1, wherein generating the plurality of points from respective patches from the plurality images annotated as one of the first type or the second type includes identifying a third subset of points of the plurality of points, and wherein the steps of clustering, identifying the first cluster, assigning the points, generating the plurality of triplets, calculating the loss function, and adjusting the parameters of the image classifier are performed based on the third subset of points, the method further comprising:
responsive to adjusting the parameters of the image classifier based on the third subset of points, repeating the steps of clustering, identifying the first cluster, assigning the points, generating the plurality of triplets, calculating the loss function, and adjusting the parameters of the image classifier using a fourth subset of points of the plurality of points.

15. A system for training a model for image classification, the system comprising a device having one or more processors configured to:
generate a plurality of points from respective patches generated from a plurality of images, each image of the plurality of images annotated as one of a first type or a second type, the plurality of images having a first subset of images annotated as the first type and a second subset of images annotated as the second type, the plurality of points comprising a first subset of points corresponding to points generated from the first subset of images and a second subset of points corresponding to points generated from the second subset of images;
select, from the plurality of points, the second subset of points generated from the second subset of images annotated as the second type for clustering;
cluster, using a clustering algorithm, each point of the second subset of points selected from the plurality of points into two clusters;
identify a first cluster of the two clusters having points that are closer to the first subset of points corresponding to the first subset of images annotated as the first type than points of a second cluster of the two clusters;
assign the points in the first cluster to a class positive, the points in the second cluster to a class negative, and the first subset of points corresponding to the first subset of images annotated as the first type to an anchor class;

generate a plurality of triplets, each triplet including one of the first subset of points from the anchor class, one of the points from the class positive, and one of the points from the class negative;

calculate a loss function of the plurality of triplets; and adjust parameters of an image classifier based on the loss function.

16. The system of claim 15, wherein each patch is represented by image data in a multi-dimensional space, the device further configured to generate the plurality of points by converting the image data for each of the patches to a lower-dimensional space using the image classifier.

17. The system of claim 15, wherein the image classifier is implemented as a convolutional neural network.

18. The system of claim 15, wherein:

each image corresponds to a respective pathology slide;

the images annotated as the first type are identified as benign; and the images annotated as the second type are identified as tumorous.

19. The system of claim 15, wherein the device is further configured to:

receive image data corresponding to the plurality of images; and generate the plurality of points from respective patches of the images for only a subset of the plurality of images.

20. The system of claim 15, wherein the device is further configured to calculate the loss function of the plurality of triplets by calculating a triplet margin error for the plurality of triplets.

* * * * *